(12) United States Patent  (10) Patent No.: US 7,819,285 B2
Mochizuki et al.  (45) Date of Patent: Oct. 26, 2010

(54) COUNTER MECHANISM OF FEEDING DEVICE AND FEEDING DEVICE USING SUCH COUNTER MECHANISM

(75) Inventors: Seiji Mochizuki, Iwakuni (JP); Dai Kawada, Odawara (JP); Yoshitaka Tsuji, Osaka (JP); Shigeto Ogino, Osaka (JP); Hitoshi Toyonaga, Kawanishi (JP); Hirofumi Henmi, Osaka (JP); Masatake Yamano, Osaka (JP)

(73) Assignee: Teijin Pharma Limited, Tokyo (JP)

( * ) Notice: Subject to any disclaimer, the term of this patent is extended or adjusted under 35 U.S.C. 154(b) by 713 days.

(21) Appl. No.: 11/660,056

(22) PCT Filed: Aug. 12, 2005

(86) PCT No.: PCT/JP2005/015112

§ 371 (c)(1),
(2), (4) Date: Sep. 12, 2007

(87) PCT Pub. No.: WO2006/016726

PCT Pub. Date: Feb. 16, 2006

(65) Prior Publication Data

US 2008/0105702 A1  May 8, 2008

(30) Foreign Application Priority Data

Aug. 12, 2004 (JP) ............................. 2004-235415

(51) Int. Cl.
*B67D 7/22* (2010.01)
(52) U.S. Cl. ...................... 222/36; 222/23; 222/189.06; 222/631; 128/200.22; 128/205.23
(58) Field of Classification Search ................... 222/36, 222/23, 38, 48, 189.06, 189.11, 325, 630–633; 128/200.23, 200.22, 200.24, 200.18, 200.14, 128/205.23

See application file for complete search history.

(56) References Cited

U.S. PATENT DOCUMENTS 4,565,302 A * 1/1986 Pfeiffer et al. ................ 222/38

(Continued)

FOREIGN PATENT DOCUMENTS

JP 8-505290 A 6/1996

(Continued)

OTHER PUBLICATIONS

EP Communication, dated Jun. 22, 2009, issued in corresponding EP Application No. 05780427.0, 4 pages.

*Primary Examiner* — Frederick C. Nicolas
(74) *Attorney, Agent, or Firm* — Sughrue Mion, PLLC

(57) ABSTRACT

In a counter mechanism of a feeding device, in each discrete feeding operation, an amount corresponding to single delivery unit of stored material is ejected and providing a simple construction and permitting the remaining amount of stored material in the device invisible from outside to be known by counting the number of delivered units of stored material. A counter mechanism of this invention comprises a fixed member (10) fixed to the body and having cam lobes formed in circumferential direction, a gear (20) having a count number display that can be monitored from the outside, a rotating member (40) being restricted to rotate either to a position in the rotating direction to allow feeding of a single delivery unit and a position to preventing feeding of the stored material, a ring member (30) which can rotates in interlock with the rotating motion of the rotating member and comprises a resiliently deformable cam follower having a jaw formed at a predetermined position in circumferential direction. The rotating member is operated for a single feeding operation, the jaw of the resilient cam follower is engaged with the gear so as to rotate the gear and increase the count by only one in the count number display.

14 Claims, 13 Drawing Sheets

U.S. PATENT DOCUMENTS

| | | | |
|---|---|---|---|
| 5,349,945 A * | 9/1994 | Wass et al. | 128/200.23 |
| 5,482,030 A * | 1/1996 | Klein | 128/200.23 |
| 5,988,496 A | 11/1999 | Bruna | |
| 6,240,918 B1 | 6/2001 | Ambrosio et al. | |
| 6,435,372 B1 * | 8/2002 | Blacker et al. | 222/23 |
| 6,679,251 B1 | 1/2004 | Gallem et al. | |

FOREIGN PATENT DOCUMENTS

| | | |
|---|---|---|
| JP | 10-501357 A | 2/1998 |
| WO | WO 92/00771 A1 | 1/1992 |
| WO | WO 95/34874 A1 | 12/1995 |
| WO | 01/31578 A1 | 5/2001 |
| WO | 2004/026380 A2 | 4/2004 |

* cited by examiner

Fig.5
(a)
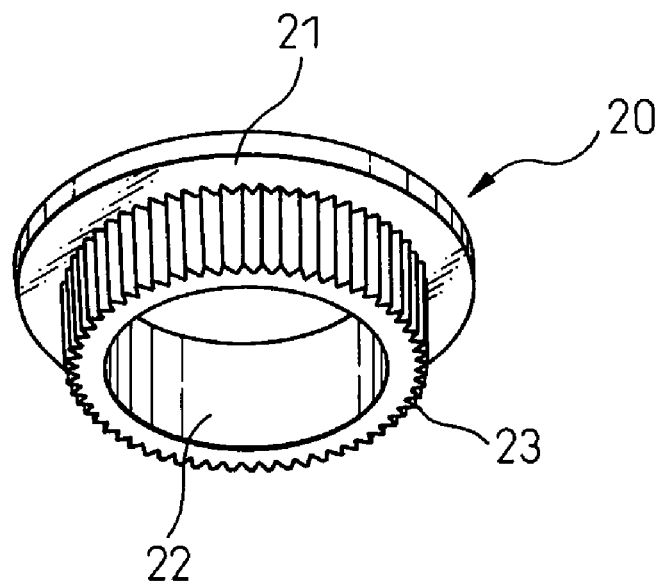
(b)
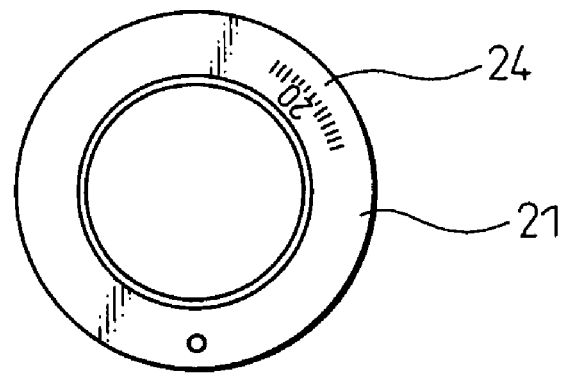

US 7,819,285 B2

COUNTER MECHANISM OF FEEDING DEVICE AND FEEDING DEVICE USING SUCH COUNTER MECHANISM

TECHNICAL FIELD

The present invention relates to a counter mechanism used in a feeding device for feeding powdered, liquid, or the like, and to a feeding device comprising such a counter mechanism.

BACKGROUND OF ART

A powdered medicine multiple dose metered feeding device capable of administering multiple doses each having a predetermined amount of powdered medicine has been conventionally known (see, for example, Patent Document 1). This device has the construction as described below: Under the bottom surface of a medicinetorage chamber capable of storing powdered medicine for plural times of administering operation, there is provided a medicine container chamber capable of containing the powdered medicine for single delivery unit corresponding to single administering operation. A medicine guiding section kept in contact with the bottom surface of the medicinetorage chamber, is movable between a filling position and an administering position. At the filling position, it opens the medicine container chamber to the medicinetorage chamber, and at the administering position, it closes the medicine container chamber to the medicinetorage chamber, and at the same time, allows the medicine container chamber to communicate with the exterior of the device via a tube. When the medicine guiding section is at the filling position, the powdered medicine in the storage chamber is filled into the medicine container chamber, and while the medicine guiding section is being moved from the filling position to the administering position, the powdered medicine in the container chamber is metered by level measuring to a single delivery unit corresponding to a single administering operation, and at the administering position, operates a pump unit so as to send air via a filter into the container chamber to thereby eject the powdered medicine in the container chamber together with air through a tube out of the device.

The device disclosed in Patent References 1 and 2 has several advantages in that it requires only rotating operation and pumping operation to administer a predetermined amount of powdered medicine precisely by atomizing and inhaling, and therefore is easy to be operated in use, and convenient to be carried and is relatively cheap in manufacturing cost.

However, this device has no counter mechanism for displaying the number of administering operations of the powdered medicineo that it is sometimes difficult to know the amount of the powdered medicinetored in the device.

Also, a powdered medicineuction device having a counting mechanism has been also known (for example, Patent Documents 3-5). The counting mechanism disclosed in Patent Document 3 is characterized in that a pawl is engaged by a spring with either one of two gears having a common shaft, but having different depths, and these two gears are moved at the different interval with rotating motion. However, many parts are necessary and the structure is rather complicated. In a counting mechanism disclosed in Patent Document 4, a rotational operation of a suction device for spraying is to be cooperated with two gears having count display by means of two gears having different shafts. However, many parts are necessary and the structure is also complicated. In a counting mechanism disclosed in the Patent Document 5 is characterized in that a propeller-shaped actuator is moved in the up and down-ward is converted to rotating motion of the counter by means of a gear which is mechanically engaged with the propeller. Although this mechanism is not so complicated, it is not so suitable to a device in which the medicine filling operation can be done by a rotating motion, such as disclosed in the Patent-Document 1.

Patent Document 1: WO 00/41755 Specification
Patent Document 2: WO 01/95962 Specification
Patent Document 3: U.S. Pat. No. 2,924,924
Patent Document 4: WO 05/002654
Patent Document 5: WO 02/091293

DISCLOSURE OF INVENTION

It is an object of the present invention to provide a counter mechanism of a feeding device having simple construction and capable of indicating the remaining amount of stored material in the interior of the device that is invisible from outside by counting the number of feeding operations performed of the stored material, and a metered feeding device comprising such a counter mechanism.

In order to attain above object, in accordance with the present invention, there is provided a counter mechanism of a feeding device for feeding to the outside, in each discrete feeding operation, an amount corresponding to single delivery unit of stored material which has been stored in a storage chamber, the counter mechanism comprising: a fixed member which is fixed to the device body and having a first contact portion formed at a predetermined position in circumferential direction thereof; a gear having a count number display that can be monitored from the outside; a rotating member being restricted to rotate either to a position in the rotating direction to allow feeding of a single delivery unit and a position to preventing feeding of the stored material; a ring member which can rotates in interlock with the rotating motion of said rotating member and comprises a second contact portion formed at a predetermined position in circumferential direction thereof; one of the first and second contact portions comprising a resiliently deformable cam follower having a jaw and the other being a cam being engagable with the can follower, and the gear being controlled to rotate in such a manner that, during the rotating member rotate for a single delivery unit, due to the mutual operation of the cam and cam follower, the jaw is engaged with the gear to rotate the gear only by a single gage in the count number display.

In a counter mechanism as mentioned above, (in a case that the rotating member is rotated only in the positive direction) the rotating member is mounted to be able to rotate only in the positive direction, in the operation of positive rotation, the rotating member can take either a first position in the rotating direction at which feeding of a single delivery unit of the stored material is allowed and a second position at which delivery of the stored material is prevented, during the rotating member moves from the first position to the second position and again from the second position to the first position, the gear is rotated only by a single gage in the count number display.

Otherwise, in a counter mechanism as mentioned above, (in a case that the rotating member is reciprocally rotated in the positive and reverse directions), the rotating member is rotatable within a range of a predetermined angle between a first position in the rotating direction at which feeding of a single delivery unit of the stored material is allowed and a second position at which delivery of the stored material is prevented, during the rotating member moves for one stroke between the first position and the second position, the gear is rotated only by a single gage in the count number display.

In either case that the rotating member is rotated only one direction, or the rotating member is reciprocally rotated in the positive and reverse directions, the following structure can be applied.

a) the first contact portion of the fixed member is a cam follower and the second contact portion of the ring member is a cam.

b) contrary, the first contact portion of the fixed member is a cam and the second contact portion of the ring member is a cam follower.

In addition, in either of a) or b) the following structure can be applied.

c) the ring member comprises a protrusion being engaged with the gear to prevent the gear from an idling movement thereof except when the gear is moved during the count number display is changed.

d) contrary, the fixed member comprises a protrusion being engaged with the gear to prevent the gear from an idling movement thereof except when the gear is moved during the count number display is changed.

In addition, in either case, the gear is ring-shaped and comprises a cylinder having an outer surface provided with teeth and a flange integrally formed with the cylinder having a count number display, the rotating member comprising a nozzle for the feeding device, a cylinder having a diameter larger than that of the nozzle and adaptable to be rotated for operating the device, and a disc plate integrally formed with and connecting the nozzle and the cylinder and having a window capable of viewing the count number display from the outside through the window.

In this case, the count number display is formed on a face of the flange opposite to the cylinder and the window is provided in the disc plate. In this case, a thin plate having a small opening for viewing the count number display is disposed between the rotating member and the flange.

Otherwise, the count number display is formed on a outer wall surface of the flange, the window is provided in the cylinder of the rotating member.

Also, in the present invention, there is provided a feeding device including the counter, comprising: a storage chamber capable of storing multiple delivery units of stored material; a container chamber provided on a portion of wall of said storage chamber and capable of containing single delivery unit of the stored material; a stored material delivery unit in which container chamber is allowed to be filled with a single delivery unit of the stored material when a rotating member is in the filling position, and the single delivery unit of the stored material is allowed to be ejected to the outside when the rotating member is in the ejecting position, and a pump attached to and connected with the container at the opposite side of the storage chamber through a filter.

In this feeding device, the container chamber is provided under the bottom of the storage chamber, the stored material delivery unit is rotated together with the rotating member so as to be movable between the filling position and the ejecting position, while being kept in contact with a bottom surface of the storage chamber, at the filling position, the container chamber is opened relative to the storage chamber by opening an opening means of the stored material delivery unit to allow the container chamber being filled with the stored material from the storage chamber, and at the ejecting position, the container chamber is closed relative to the storage chamber, but communicated with a nozzle formed in the rotating member via a delivery passage of the stored material delivery unit, so that a single delivery unit of stored material in the container chamber is allowed to be ejected to the outside through the delivery passage and the nozzle.

In addition, a bottom wall of the storage chamber has a hole communicated with the pump and at the filling position the hole communicate the pump to the outside through the delivery passage of the stored material delivery unit and the nozzle of the rotating member and at the ejecting position the hole is closed by the stored material delivery unit. In this case, the counter mechanism of this invention can also be applied to that disclosed in WO01/95962 (Patent document 2) as mentioned above in which a bottom wall of a storage chamber has a pressure release hole).

The counter mechanism of the present invention is capable of exhibiting counting function by means of rotating action, and the counting function can be achieved by said rotating action performed as positive rotation only as well as in combination of positive and reverse rotations.

The rotating action occurs when a single delivery unit of the stored material is metered in the metered feeding device which stores multiple delivery units of the stored material. By means of a counter mechanism interlocked with the rotating action that occurs in metering the stored material, the number of delivery units fed by the device can be counted.

A metered feeding device capable of metering and feeding a single delivery unit of stored material can be found in those disclosed in WO 00/41755 Specification, WO 01/95962 Specification, Japanese Patent Publication No. 2003-175103, or Japanese Patent Publication 2003-175093. It should be noted that the counter mechanism of this invention can of course be applied to such a feeding device in which a bottom wall of a storage chamber has no pressure release hole, contrary to the feeding device disclosed in WO01/95962 (Patent document 2) provided with a pressure release hole at the bottom wall of storage chamber.

The stored material of the present invention may be of any nature or form as long as it can be stored in an amount corresponding to multiple delivery units and can be metered and fed each time as a single delivery unit. Examples of such stored material include foods, healthy foods, and medicine. The form of such stored material may be solid form such as powdered, granules, and fine particles, or may be liquid form. When the stored material is to be ejected by means of air pressure, preferable form includes powdered, and when the stored material is to be discharged by tilting or inverting the device, preferable form is liquid.

The foods include seasonings, spices, and the like. Further, as required, the medicine may be suitably blended with known additives such as stabilizers, anti-oxidants, or the like.

The healthy foods include supplements represented by vitamins, nutrients, and the like. Further, as required, the medicine may be suitably blended with known additives such as stabilizers, anti-oxidants, or the like.

The medicine may be constituted by, for example, a medicine and a widely known excipient such as milk sugar, starches, celluloses or polyvinyl polymer, or may be constituted by a medicine alone. Further, as required, the medicine may be suitably blended with known additives such as stabilizers, anti-oxidants, or the like.

Such medicine are preferably externally administered medicine, and more specifically, orally, intranasally, intraocularly, inhalationally, rectally, or intravaginally administered medicine.

As the medicine to be used for the present invention, a wide variety of medicine can be used. Specific examples include non-peptide/proteinaceous medicineuch as steroidal anti-inflammatory medicine or non-steroidal anti-inflammatory medicine, analgesics anti-inflammatory medicine, tranquilizers, anti-depressants, cough suppressants and expectorants, anti-histamic agents, anti-allergic agents, nausea suppressing agents, anti-insomnia medicine, vitamins, sex hormones, anti-neoplastics, anti-arrhythmias, anti-hypertensive agents, anxyolytic sedatives, anti-psychotics, anti-gastric ulcer medicine, heart failure treating medicine, analgesics, bronchodilators, obesity treating agents, platelet coagulation suppressing agents, anti-diabetics, muscle relaxants, anti-migraines and anti-rheumatoid arthritis medicine, antibiotics, vasoconstrictors, etc. Peptide/proteinaceous medicineuch as hormones, cytocains, antibodies, vaccines, as well as nucleic acids such as anti-sense and genes can also be used.

BRIEF DESCRIPTION OF THE DRAWINGS

FIG. 5 is a perspective view (a) showing a gear and a plan view (b) showing the gear from flange side;

BEST MODE FOR CARRYING OUT THE INVENTION

Now, the present invention will be described in detail below with reference to appended drawings showing embodiments thereof.

Figure 1:
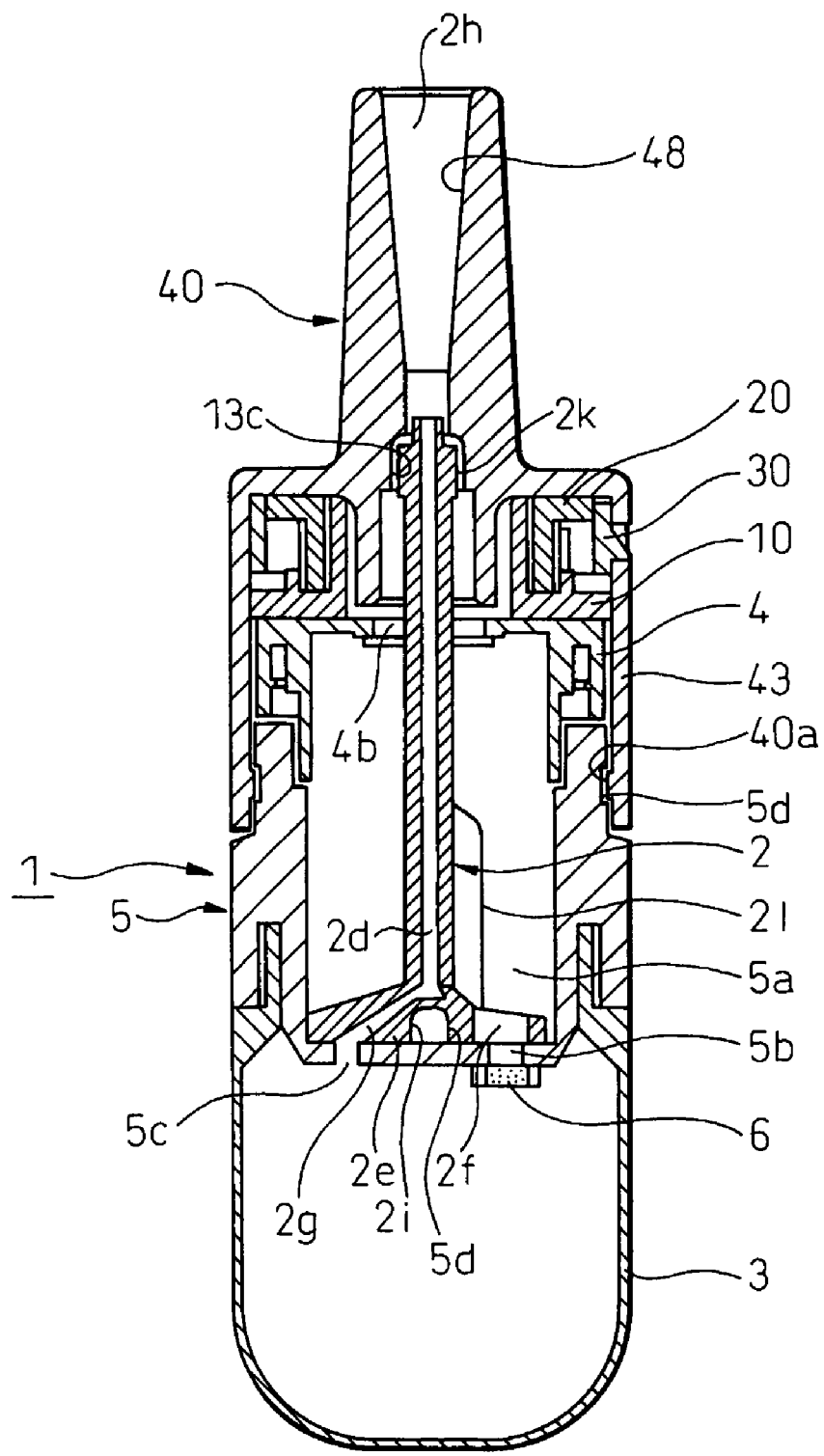
FIG. 1 is a sectional view showing a metered feeding device having a counter mechanism according to the present invention.
Figure 2:
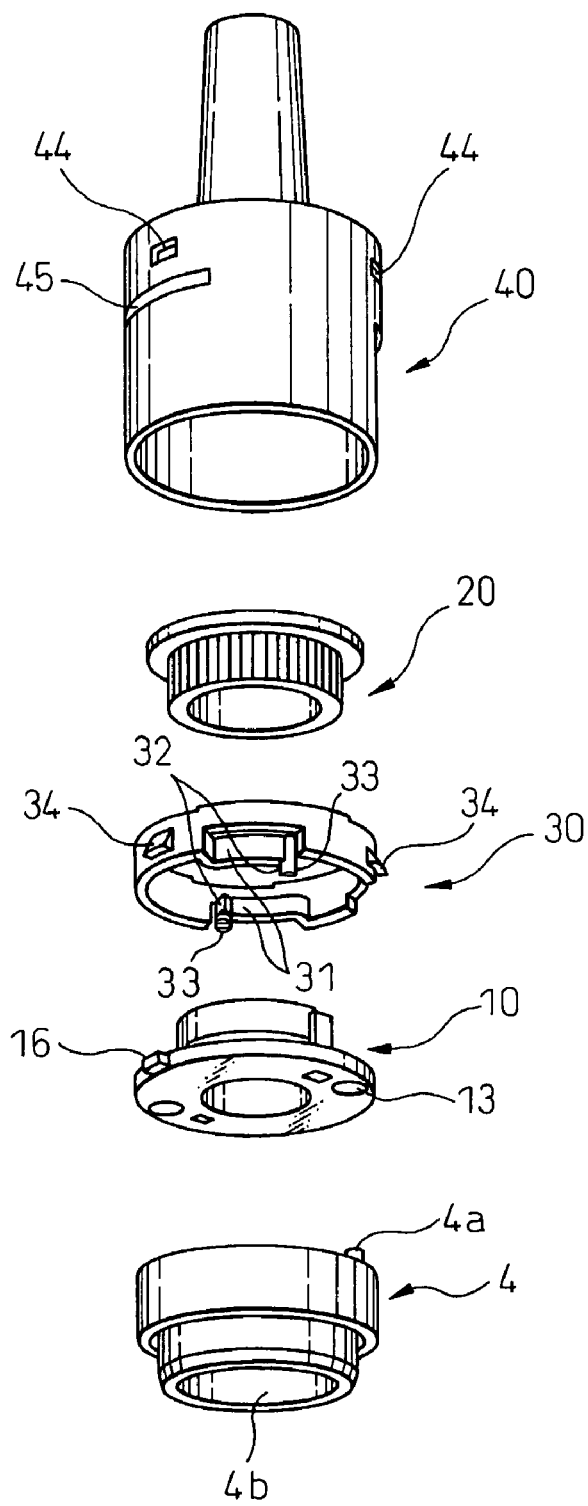
FIG. 2 is an exploded perspective view showing the counter mechanism according to the present invention.

FIG. 1 is a view showing a powdered medicine feeding device comprising a counter mechanism of the present invention. FIG. 2 is an exploded perspective view showing a portion, mainly the counter mechanism of the first embodiment, of the delivery device, and shows the parts constituting the counter mechanism.

Figure 3:
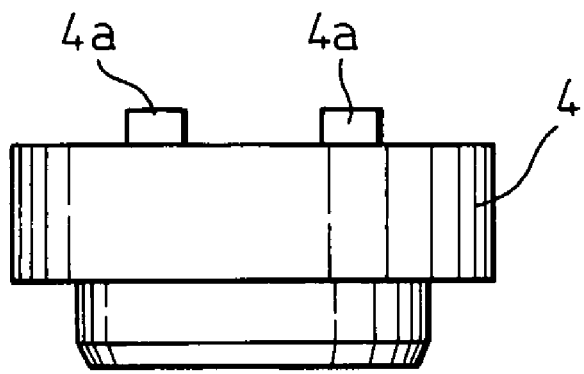
FIG. 3 is a front view showing a closure section.
Figure 4:
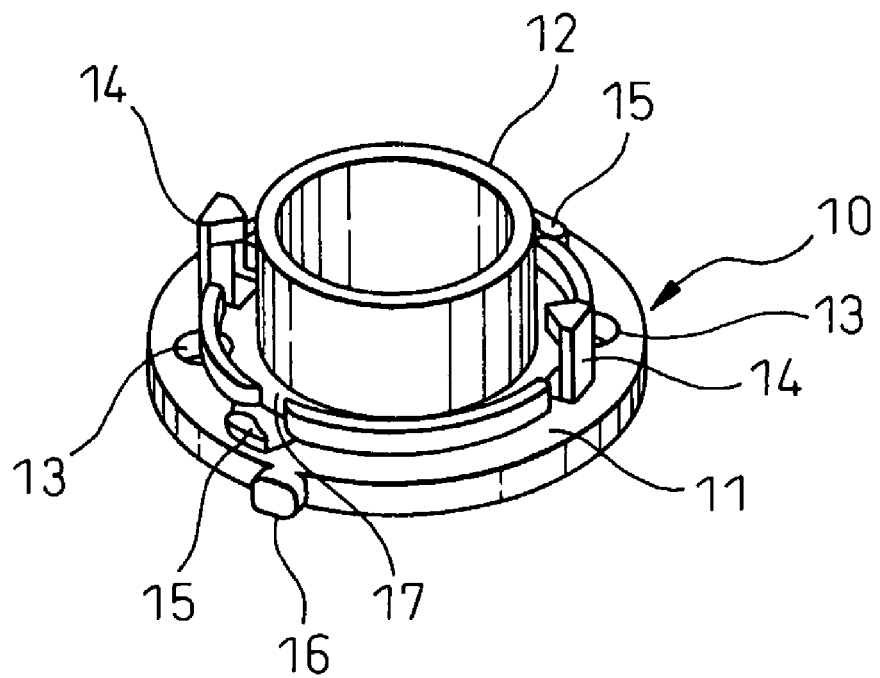
FIG. 4 is a perspective view showing a fixed stage.
Figure 6:
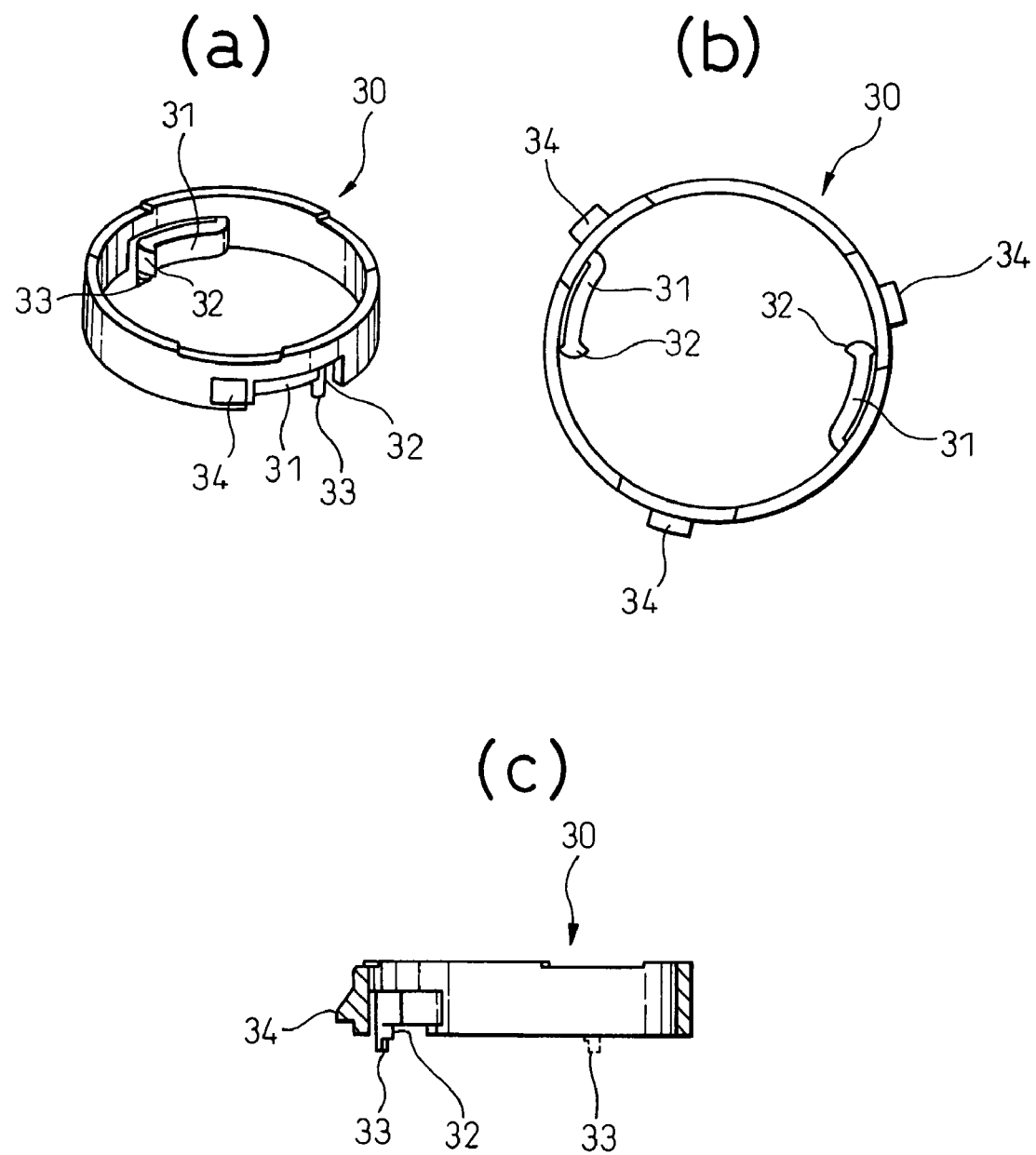
FIG. 6 is a perspective view (a), a plan view (b) and a sectional view (c) showing a ring member.
Figure 7:
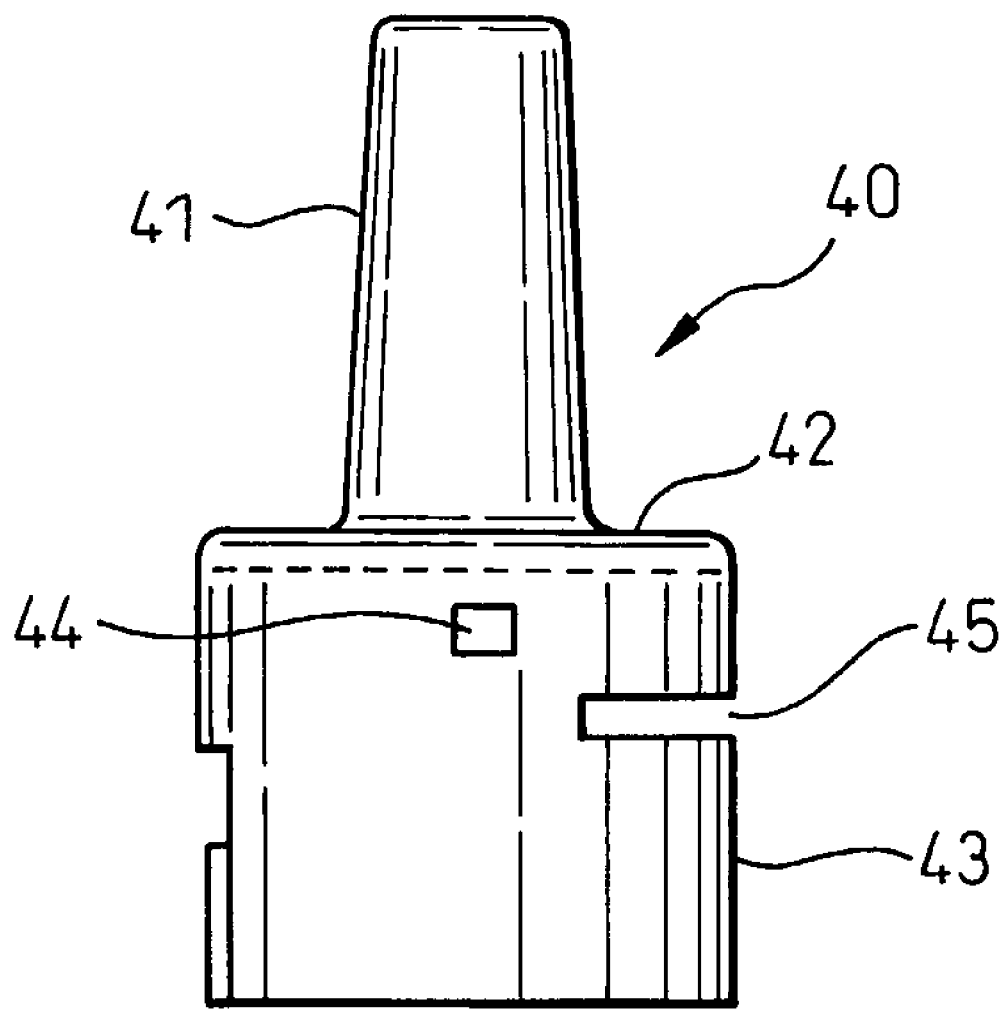
FIG. 7 is a front view showing a rotating member.

First, the counter mechanism of the first embodiment will be described. FIG. 3 is a view showing a closure section of the device body, and FIGS. 4-7 are views showing respective constituent parts of the counter mechanism. FIG. 4 shows a fixed stage, FIG. 5 shows a gear, FIG. 6 show a ring member, and FIG. 7 shows a rotating member.

The closure section 4 shown in FIG. 3 is a part constituting a closure of the chamber body for storing the powdered of the powdered metered feeding device to be described later, and constitutes a portion of the device body. A pair of protrusions 4a protruding upward are provided on the top surface of the closure section 4 at positions opposing to each other at angular separation of about 180°.

The ring-shaped fixed stage 10 shown in FIG. 4 has the flange section 11 and cylinder section 12 integrally formed in one unit from suitable resin or the like, with a pair of holes 13 provided on the flange section 11 at positions opposing to each other at angular separation of about 180°.

The fixed stage 10 is fixed so as to be not rotated on the closure section 4 with a air of holes 13 fitted to a pair of protrusions 4a of the closure section 4.

On the flange section 11 of the fixed stage 10, a pair of protrusions 14 are provided at positions opposing to each other at angular separation of about 180° for preventing the gear 20 to be described later from running idle, and extend generally in parallel to the cylinder section 12 with the distal ends of these protrusions directed radially inward. Also, a pair of cam lobes 15 are provided on the flange section 11 of the fixed stage 10 at positions opposing to each other at angular separation of about 180° for cooperating with resilient sections 32 of a ring member 30 to be described later to compose a cam mechanism. Further, a protrusion 16 for fitting to a slit 45 of a rotating member 40 to be described later is provided so as to project outward on the outer periphery of the flange section 11 of the fixed stage 10.

A pair of cam grooves 17 are provided radially inwardly, opposite to the pair of cam lobes 15. As described later, when the jaws 32 of the ring member 30 come into contact with the came lobe 15, move radially inward along the cam grooves 17 and come into engage with the teeth of the gear 20.

A ring-shaped gear 20 shown in FIG. 5 is formed in one unit from suitable resin or the like, and is composed of a flange section 21, an inner cylinder section 22, and an outer gear teeth 23, with the inner cylinder 22 being rotatably fitted to the cylinder section 12 of the fixed stage 10. However, while the gear 20 is fitted to the fixed stage 10, a pair of protrusions 14 of the fixed stage 10 are lightly in contact with or fitted to the outer gear teeth 23 so as to prevent the gear 20 from slipping and running idle relative to the fixed stage. The surface of the flange portion 21 opposite to the outer teeth 23 is provided with an indicating gage 24 in the circumferential direction for indicating the number of times for feeding the medicine.

A ring member 30 shown in FIG. 6 is integrally formed in generally ring-like shape from suitable resin, and has a pair of resilient sections 31 at an angular separation of about 180°, projecting a little on inner circumference of the ring and extending for a specified distance along the circumferential direction. Each resilient section 31 has a claw section 32 projecting inward at the distal end, and in addition, has a cam follower section 33 projecting a little downward under the claw section 32. The pair of resilient sections 31 are elastically deformable relative to the ring member 30, and the cam follower sections 33 cooperate with the pair of cam lobes 15 of the fixed stage 10 to compose a cam mechanism.

The ring member 30 has, in addition, a plurality of protrusions 34, for example, three protrusions 34 formed at equal circumferential separation as shown in the Figure, projecting outward on the outer periphery. These protrusions 34 are fitted to holes 44 in the rotating member to be described later so as to rotate the ring member 30 together with the rotating member 40. The number of protrusions 34 is not restricted as far as the ring member 30 and the rotating member 40 can be rotated simultaneously. For example, the number may be one or two. The slit 45 for limiting the rotating range of the rotating member 40, in this embodiment, is provided in the cylindrical portion 43 of the rotating member 40. However, the slit 45 can be provided at the disc portion 42 of the rotating member 40 and, on the other hand, the protrusion 16 of the fixed stage 10 may be arranged at a position to allow the same function.

The closure section 4, the fixed stage 10, the gear 20, the ring member 30 and the rotating member 40 are assembled together on concentric circles. The assembled state is shown on the upper part of FIG. 1. The closure section 4 is fitted and fixed onto the body 1, and the protrusion 4a on the inner circumference of the rotating member 40 is rotatably fitted to the peripheral groove 5d of the chamber body 5 with the fixed stage 10, the gear 20 and the ring member 30 disposed between the closure section 4 and the rotating member 40, each parts being fixed so as not to move in axial direction.

In the assembled state, as described above, the slit 45 of the rotating member 40 is fitted to the protrusion 16 of the fixed stage 10 and the fixed stage 10 is secured to the closure section which is secured to the medicine storage section 5 such that the rotating member 40 can rotate relative to the fixed stage 10, and hence relative to the chamber body 5, within the specified angular range defined by the slit 45.

Since the ring member 30 has three peripheral protrusions 34 fitted to the three corresponding holes 44 of the rotating member 40, it rotates with the rotating member 40 in one unit.

Thus, while the rotating member 40 rotates within the specified angular range from the first position (filling position) at which a single delivery unit of powdered medicine is permitted to be ejected to the second position (ejecting position) at which feeding of powdered medicine is inhibited, the ring member 30 similarly rotates relative to the fixed stage 10 within the same angular range.

Next, counting operation for rotating the gear 20 for one graduation to increase the count display while the ring member 30 rotates from the first position to the second position and from the second position back to the first position, will be described.

For example, when the ring member 30 rotates from the first position to the second position, the cam follower section 33 at the distal end of the resilient section 31 abuts against the cam lobe 15 of the fixed stage 10 so that the claw section 32 at the distal end of the resilient section 31 is pressed radially inward. At this point, the claw section 32 is engaged with the outer gear teeth 23 of the gear 20 in the guide groove 17 of the fixed stage 10. The gear 20 is rotated by the claw section 32 against the resistance of the protrusion 14. When the gear 20 is rotated for one gear tooth or for one graduation, the cam follower section 33 at the distal end of the resilient section 31 is on opposite incline surface of the cam lobe 15 of the fixed stage 10, and the claw section 32 is returned radially outward and the claw section 32 is disengaged from the outer gear teeth 23 of the gear 20. Since the gear 20 is prevented from running idle by the protrusion 14 of the fixed stage 10, it can rotate only for one gear tooth or for one graduation.

Next, when the ring member 30 is returned from the second position to the first position, the cam follower section 33 at the distal end of the resilient section 31 reaches the cam lobe 15 of the fixed stage 10. This time, although it comes into contact with the opposite surface of the cam lobe 15, the cam follower section only goes over the cam lobe 15. Thus, the claw section 32 at the distal end of the resilient section 31 is displaced somewhat only in the axial direction of the ring member 30, but not in the radial direction, so that the claw section 32 does not come into engagement with the outer gear teeth 23 of the gear 20. Therefore, the gear 20 remains prevented by the protrusion 14 of the fixed stage 10 from running idle.

In this manner, the gear 20 is rotated for increment of one graduation only when the ring member 30 moves from the first position (filling position) to the second position (ejecting position). It is also possible to construct the mechanism such that the gear 20 is rotated for increment of one graduation only when the ring member 30 moves from the second position (ejecting position) back to the first position (filling position) and remains stopped in rotation when the ring member 30 moves from the first position to the second position.

Figure 15:
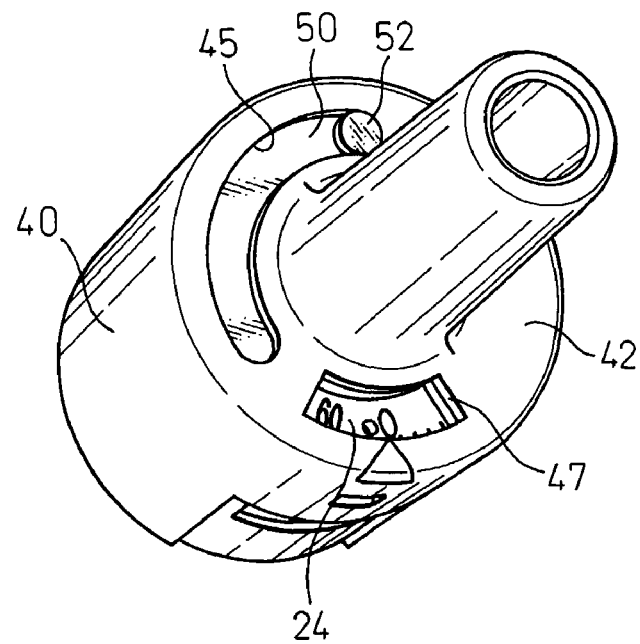
FIG. 15 is a view showing an indicating dial viewed from the above.

Each time operation for one round is completed by moving the ring member 30 from the first position (filling position) to the second position (ejecting position) to eject a single delivery unit of powdered for one operation, and then moving the ring member 30 from the second position (ejecting position) back to the first position (filling position), the gear 20 is rotated for one graduation. By providing a display such as a scale 24 as shown in FIG. 5(b), for example, on the ring-shaped surface on the opposite side to the outer gear teeth 23 of the flange section 21 of the gear 20, the scale can be monitored from outside, via a window (not shown) of the disc section 42 of the rotating member 40, for example, and the number of delivered units of the powdered medicine in the storage chamber of the device (FIG. 15).

Figure 16:
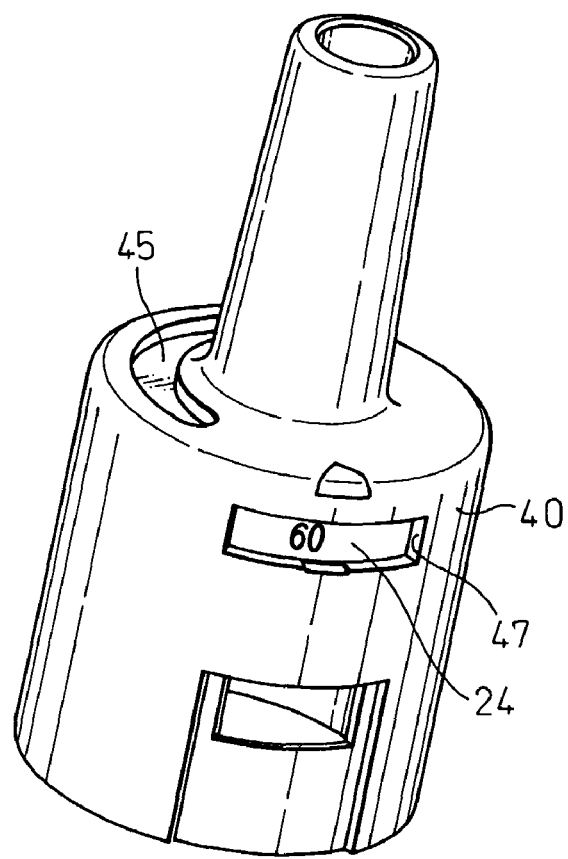
FIG. 16 is a view showing an indicating dial viewed from the side.

As shown in FIG. 16, it is also possible to provide a gage on the side face of the flange portion 21 of the gear 20 monitored from the side of the rotating member 40.

The feeding device of the present invention will now be described with reference to FIG. 1. Basically, as described above, a feeding device, such as the "multi-dose powdered medicine administering device" disclosed in WO00/41755 Specification, WO01/95962 Specification, JP-A 2003-175103, JP-A 2003-175093, can be applied to the feeding device of this invention.

As an embodiment of the feeding device, a medicine feeding device will be described with reference to FIG. 1.

A body 1 is constituted by a closure 4 and a medicinetorage unit 5. The medicinetorage unit 5 is constituted by a cylindrical wall and a bottom wall, is integrally formed of resin or the like, and is opened at the top. The interior thereof is defined by a medicinetorage chamber 5a capable of storing the powdered medicine in an amount for administering the medicine many times, and a medicine container chamber 5b formed in the bottom surface of the medicinetorage chamber and having a content for administering the powdered medicine one time. A filter 6 being fitted to the bottom surface of the medicine container chamber 5b to permit the passage of the air but inhibiting the passage of the powdered medicine, the filter serving as an air communication port communicated with the pump unit 3 so that the air is blown in upon depressing and relaxing the pump unit 3 at the time of guiding the medicine.

The closure unit 4 has a hole 4b at the center thereof for communicating the medicine guiding unit 2 with said body 1. The interior of the medicinetorage chamber 5a is hermetically sealed with the closure unit 4, medicinetorage unit 5 and said medicine guiding unit 2.

The medicine guiding unit 2 is integrally formed of resin or the like and comprises a rod-like portion vertically extending through the center of the medicinetorage chamber 5a of the body 1 and defining therein an air passage 2d for the powdered medicine or the air. There is a projection protruding upward at the bottom surface of the medicine container chamber 5b and, on the other hand, there is a recess at the center of the bottom disc portion of the medicine guiding unit 2, which are engaged with each other, so that the medicine guiding unit 2 is rotatably disposed in the medicine container chamber 5b.

The bottom disc portion of the medicine guiding unit 2 has a hole 2f of a diameter larger than that of the medicine container chamber 5b for communicating the medicinetorage chamber 5a with the medicine container chamber 5b. The bottom surface 2e of the medicine guiding unit 2 rotates while being in contact with the bottom surface of the medicine container chamber 5b, the powdered medicine in the medicinetorage chamber 5a is allowed to flow into the medicine container chamber 5b and, on the other hand, or is interlocked between the medicinetorage chamber Sa and the medicine container chamber 5b.

The bottom disc-portion of the medicine guiding unit 2 has at a part thereof a pipe 2g for communicating the medicine container chamber 5b with the passage 2d for permitting passage of the powdered medicine and the air blown out from the pump unit 3 through the medicine-container chamber 5b of the body 1. This pipe 2g is communicated with the passage 2d vertically extending through the center of the medicine guiding unit 2 and, thus aligned with a port 5c of the bottom wall of the medicinetorage unit 5.

A bag-like resilient deformable pump unit 3 is attached to the bottom of the medicinetorage unit 5 constituting the body 1. As described later, upon depressing and relaxing the pump unit 3, the air can be blown in or the powdered medicine can be discharged.

The rotating member 40 shown in FIG. 7 is integrally formed from suitable resin or the like including a nozzle section 41 for ejecting powdered medicine, a disc section 42, and a cylinder section 43. The nozzle section 41 has therein an air passage 48 for transmitting powdered medicine or air and a spray port 2h. As described above, the cylinder section 43 has three holes 44, for example, formed at equal separation in circumferential direction for fitting onto the protrusions 33 of the ring member 30, and further has a slit 45 extending over a specified angle in circumferential direction formed for engagement with the protrusion 16 of the fixed stage 10. The protrusion 40a formed on the inside wall of the cylinder section 43 is fitted with the groove 40a circumferentially formed in the medicinetorage unit 5 constituting the body 1. Thus, the rotating member 40 can rotate relative to the body within a specified angular range defined by the slit 45.

On the other hand, the lower angular hole 13c of the nozzle section 41 of the rotating member 40 is fitted with the upper angular shaft 2k of the medicine guiding section 2. Therefore, the rotating member 40 and the medicine guiding section 2 are simultaneously rotated.

Therefore, the rotating member 40 is rotated from the outside with respect to the body 1, the medicine guiding section 2 is rotated simultaneously with the rotating member 40 relative to the body 1 including the medicinetorage section 5, so that it can be rotated between the first position filling position) at which a single delivery unit of powdered medicine is permitted to be filled and the second position (ejecting position) at which a metered powdered medicine is permitted to be ejected.

In the first position (filling position) shown in FIG. 1, the hole 2f of the bottom surface 2e of the medicine guiding section 2 is aligned with the medicine container chamber 5b of the body 1. Thus, by communicating the medicinetorage chamber 5a with the medicine container chamber 5b, the powdered medicine in the medicinetorage chamber 5a flows down through the hole 2f of the medicine guiding section 2 and filled within the medicine container chamber 5b. In this state, the hole 5c at the bottom of the medicinetorage chamber 5a is at a position aligned with the passage 2g of the medicine guiding section at the bottom thereof.

Next, during the medicine guiding section 2 is rotated with the rotating member 40, the bottom surface 2e of the medicine guiding section 2 meters the powdered medicine on the medicine container chamber 5b so that the amount of the powdered medicine in the medicinetorage chamber 5a be a predetermined value. Also, since the medicine guiding section 2 is rotated with the rotating member 40, the medicine container chamber 5b becomes to the second position (ejecting position) to communicate with the passage 2g, air passage 2d and spray port 2h. In this state, a certain amount of metered powdered medicine is ejected from the container chamber 5b through the pipe 2g and air passage 2d of the medicine guiding section 2 to spray from the spray port 2h of the rotating member 40.

After the spraying operation, during the pump unit 3 is returned back to the initial position by its elastic returning force, air flows from the outside through the spray port 2h of the rotating member 40, air passages 2d and 2g of the medicine guiding section 2 and the hole 5c of the medicinetorage section 5 into the pump unit 3.

Then, the rotating member 40 is rotated to the initial portion or the above mentioned filling position. By rotating the medicine guiding section 2 together with the rotating member 40, the blade 21 formed on the medicine guiding section 2 is rotated so that the powdered medicine in the medicinetorage section 5a can be agitated.

The metered feeding device of the present invention can be assembled in a manner as described below.

First, the filter 6 is set in position by being pushed from the outer side into the medicine container chamber 5b formed in the bottom on the outer side of the device body 1. The setting position is defined by forming a step in the medicine container chamber 5b at the time of molding the device body 1. Then, the medicine guiding section 2 is inserted in the medicinetorage chamber 5 at a position such that, for example, the medicine container chamber 5b coincides with the hole 2f formed in the medicine guiding section 2 and having a diameter larger than that of the medicine container chamber, and the hole at the center of the bottom surface 2e of the medicine guiding section 2 is fitted and secured to the protrusion at the center of the bottom surface of the device body. Here, the required amount of powdered medicine is introduced into the medicinetorage chamber 5a in the device body 1. Then, the closure section 4 is intimately adhered and secured to the device body 1 while passing the guiding section 2 through the hole 4b at the center. Next, the rotating member 40 is secured to the device body 1 via the fixed stage 10, the gear 20 and the ring member 30 that constitute the counter mechanism as described above in a manner such that the shaft 2h of a non-circular shape in cross section at the end of the guiding section 2 is brought into agreement with the non-circular hole 13c of the rotating member 40. It is desired that the shaft 2k and the non-circular hole 13c have a home base-like pentagonal shape in cross section having two parallel sides for exclusively determining their rotational positions, a side at right angles thereto and two sides on the opposite sides. Next, the pump unit 3) is connected and secured to the lower part of the device body 1 to thereby complete the metered feeding device of the invention.

It is also possible to attach a filter into the hole 5c in the bottom surface of the medicinetorage chamber 5a.

The pump unit 3 of the invention is an element for compressing the air to administer the powdered medicine by spraying or inhalation). It is desired that at least a portion of the flexible member or of the wall of the pump is made of a flexible material. Here, the phrase "at least a portion is made of a flexible material" means that upon pushing and relaxing a portion made of the flexible material, the powdered medicine contained in the medicine container chamber 5b can be sprayed or inhaled. This includes the cases where the whole pump unit 3 is constituted by the flexible material, and where the pump unit 3 is constituted by the flexible material except a portion near the junction portion to the device body 1 and other portions are constituted by the non-flexible material.

The metered feeding device of the present invention is constructed such that the medicine in the medicinetorage chamber 5a is transferred to the medicine container chamber 5b by rotating the medicine guiding section 2 interlocked with the rotating member 40, and a single delivery unit of medicine is metered and separated in the medicine container chamber 5b simply by rotating the medicine guiding section 2 in reverse direction. Thus, from the multiple delivery units of powdered medicinetored in the medicinetorage chamber 5a, a single delivery unit of medicine can be easily and accurately metered and separated without using a special tool such as a scraper, or without using special means for preventing density change of powdered medicine by ventilating air to avoid possible density change or deviation during storage of the powdered medicine.

In the metered feeding device of this embodiment, a decrease in the number of the parts contributes to minimizing the size of the whole device. Besides, the air passage 2d that is installed along the center axis of the medicine guiding section 2 contributes to minimizing the size (height) of the feeding device as a whole, so that it can be easily carried.

At filling position, the hole 2f in the bottom surface 2e of the medicine guiding section 2 coincides with the medicine container chamber 5b of the body 1 so that the powdered medicine is filled into the medicine container chamber 5b, and the hole 5c in the bottom surface of the medicinetorage chamber 5 coincides with the pipe 2g of the medicine guiding section 2 so that the interior of the pump unit 3 comes into communication with the exterior of the administering device and the air pressure from the pump unit 3 to the medicine container chamber 5b is reduced so as to increase the accuracy of filling the powdered medicine. When the rotating member 40 and the medicine guiding section 2 are rotated to ejecting position, the pipe 2g of the medicine guiding section 2 is communicated with the medicine container chamber 5b to permit the powdered medicine in the medicine container chamber 5b to be sprayed, and the operation is simple and easy.

In the administering device of the present invention as described above, the medicinetorage section 5 is combined with the medicine guiding section 2 and with the closure section 4 to establish a hermetically sealed state in the medicinetorage chamber 5a. Due to the hermetically sealed state, however, a difference may occur in the air pressure among the medicinetorage chamber 5a, the pump unit 3 and the exterior of the administering device at the time of filling the medicine.

In the metered feeding device of the present invention, however, the hole 5c is formed in the bottom surface of the medicinetorage chamber 5a, and is brought into agreement with the pipe 2g opened in the bottom surface of the medicine guiding section at the time of filling the medicine, enabling the air pressure to become uniform among the medicinetorage chamber 5a, pump unit 3 and exterior of the administering device. Therefore, a predetermined amount of the medicine can be metered.

Figure 8:
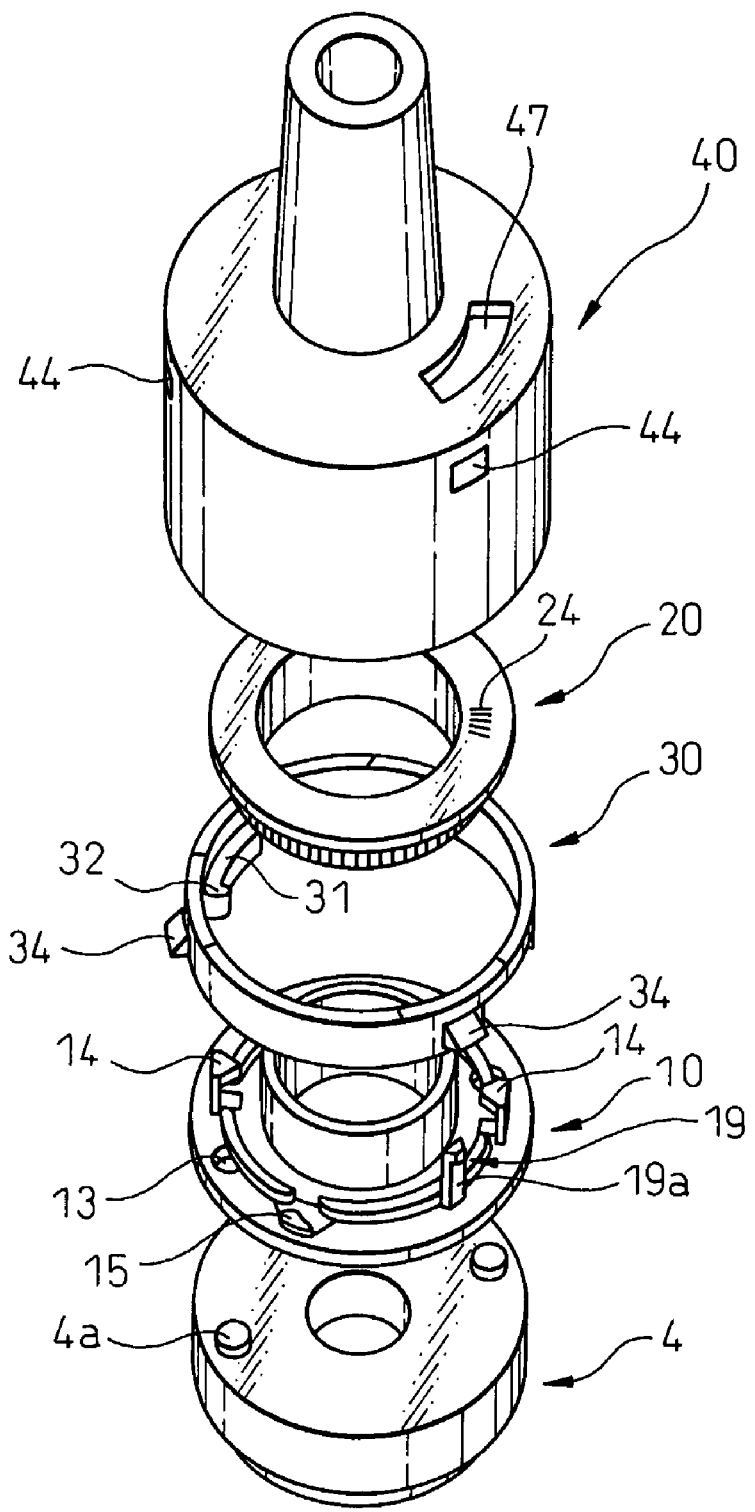
FIG. 8 is an exploded perspective view showing a counter mechanism according to the second embodiment of the present invention.

FIG. 8 is an exploded perspective view showing a counter mechanism of a feeding device according to the second embodiment of the present invention. In the previous embodiment as described above, the feeding device is constructed such that, for each operation of ejecting powdered medicine, the rotating member 40 can be rotated within the specified angular range between the first position (filling position) at which a single delivery unit of powdered medicine is metered and the second position ejecting position) at which the metered powdered medicine is permitted to be fed. In the present embodiment, in contrast, the device is constructed such that the rotating member 40 can rotate only in a specified direction (positive rotation).

As in the first embodiment, the ring member 30 rotates in one unit with the rotating member 40. In the present embodiment, however, protrusions 36 are provided at two positions opposing to each other at 180° on the inner circumference of the ring member 30 in order to regulate rotation at the first and the second positions. In correspondence to the protrusions 36, deformable ribs 19 are provided on the fixed stage 10 at two positions, so that the protrusion 36 of the ring member 30 enters into the recess 19a Of the rib 19 during positive rotation so as to regulate the rotation. When rotated in positive direction with a force exceeding the rotation regulating force, the protrusion 36 is released from the recess 19a and is enabled to rotate. After rotation of 180°, the rotation is again regulated. Thus, in the present embodiment, filling and ejecting operations are repeated at each 180°.

Therefore, in the present embodiment, aforementioned protrusion 16 on the fixed stage 10 (FIG. 4) and the slit 45 (FIG. 7) in the rotating member 40 are not provided.

During one round of operation consisting of a positive rotation from the first position (filling position) to the second position (ejecting position) and another positive rotation from the second position (ejecting position) to the first position (filling position), the claw section 32 of the resilient section 31 of the ring member 30 is engaged with the gear 20 to rotate the gear 20 for one graduation of the scale. As in the first embodiment described above, the number display of the gear 20 can be monitored, for example, through the window 47 of the rotating member 40. In this second embodiment, during the rotation of 360° of the rotating member 40 and the ring member 30 are rotated by 360°, the gear 20 is rotated by one graduation. Thus, the fixed stage 10 has only one cam lobe 15.

Figure 9:
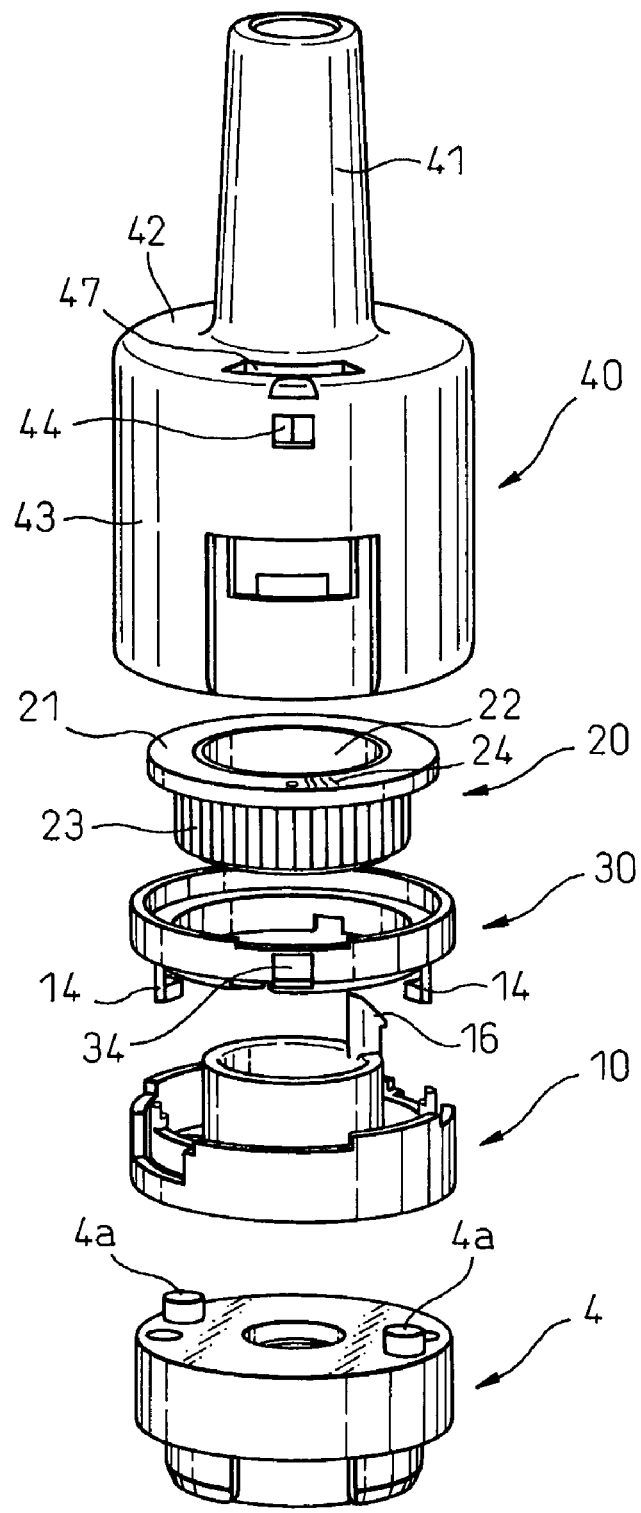
FIG. 9 is an exploded perspective view showing a counter mechanism according to the third embodiment of the present invention.
Figure 10:
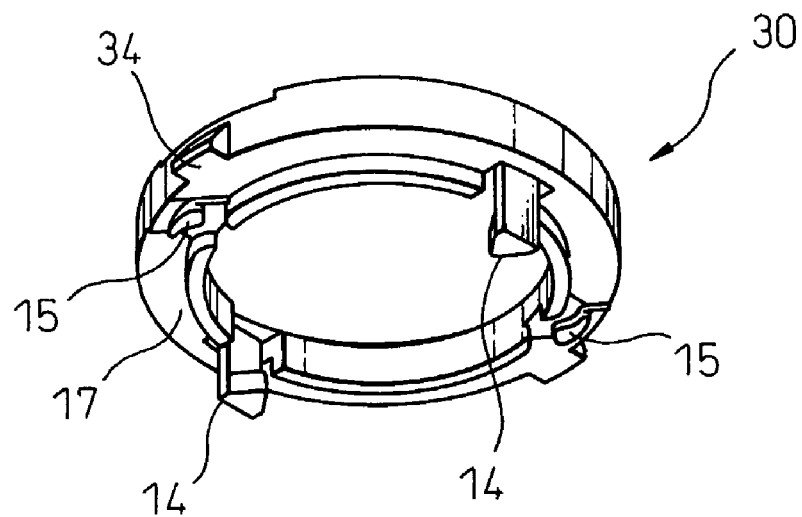
FIG. 10 is a perspective view of a ring member in the third embodiment.
Figure 11:
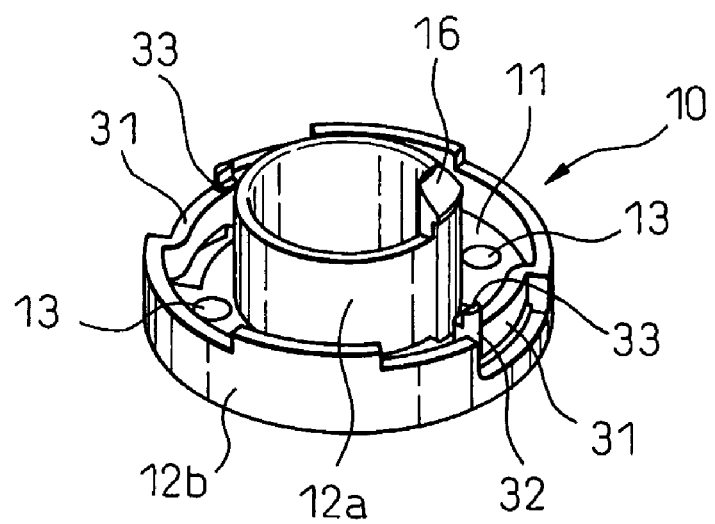
FIG. 11 is a perspective view of a fixed stage in the third embodiment.

FIG. 9 is an exploded perspective view showing a counter mechanism of a feeding device according to the third embodiment of the present invention. FIG. 10 is a perspective view of a ring member, FIG. 11 is a perspective view of a fixed stage. In each the first and second embodiment as described above, the stationary fixed stage 10 is provided with a cam base (cam lobe) and rotating ring member 30 is provided with cam follower (resilient portion 31). Contrary to this, in the third embodiment, the stationary fixed stage 10 is provided with a cam follower (resilient portion 31) and rotating ring member 30 is provided with cam base (cam lobe).

The closure section 4 is provided one or plural projections 4a protruding upward from the upper surface thereof. On the other hand, the ring-like fixed station 10 comprises a flange portion 11, an inner cylinder portion 12a and an outer cylinder portion 12a integrally molded by suitable resin or the like. The flange portion 11 has at the bottom surface thereof a recess 13 for fitting with a protrusion 4a of the closure section 4, so that the ring-like fixed stage 10 non-rotatably mounted on the closure section 4.

The inner cylinder portion 12a of the fixed stage 10 is provided with one protrusion 16 extending in the direction of the flange portion for fitting with an arch slit 45 of the disc plate 42 of the rotating member 40 as mentioned later. Also, the outer cylinder portion 12a of the fixed stage 10 is provided with a pair of resilient portions 31 arranged at 180° slightly protruding inward and extending in the circumferential direction by a certain distance. There is provided at the distal end of each resilient portions 31 with jaw portions 32 protruding inwardly and the jaw portions 32 having cam follower portions 33 slightly protruding upward. These pair of resilient portion 31 is resiliently deformable to the fixed stage 10 and the cam follower portion 33 constitutes a cam mechanism in cooperation with a pair of cam lobes of the ring member 30 mentioned later.

The ring member 30 is integrally formed by a suitable resin or the like to be a substantially ring-like shaped body provided one the outer surface thereof with two protrusions 34 arranged at 180°. These protrusions 34 are fitted with holes 44 of the rotating member 40 so that the ring member 30 is rotated together with the rotating member 40. The ring member 30 is provided with cam groove 17 in the circumferential direction and has at radially outward position of the cam groove 17 with a pair of cam lobes 15 along the cam groove 17 to guide the resilient portion 31 of the fixed stage 10, as mentioned later, in such a manner that when the jaw portion 32 of the fixed stage 10 comes into contact with the cam lobe 15, the jaw 32 is moved radially inward to be engaged with the outer teeth of the gear 20. The number of the protrusions 34 is not limited if the ring member 20 and the rotating member 40 can be rotated together, and may be two or more.

The gear 20 has the same structure as the previous embodiments, and the inner cylinder 22 being rotatably fitted to the cylinder section 12 of the fixed stage 10. However, while the gear 20 is fitted to the fixed stage 10, a pair of protrusions 14 of the ring member 30 are slightly in contact with or fitted to the outer gear teeth 23 so as to prevent the gear 20 from slipping and running idle relative to the fixed stage. The surface of the flange portion 21 opposite to the outer teeth 23 is provided with an indicating gage 24 in the circumferential direction for indicating the number of times for feeding the medicine.

The rotating member 40 is provided at its cylinder portion 43 with one or plural holes 44 fitting with the protrusions 33 of the ring member 30, and further has a slit 45 extending over a specified angle in circumferential direction formed for engagement with the protrusion 16 of the fixed stage 10.

Thus, the rotating member 40 can rotate relative to the fixed stage 10 within a specified angular range defined by the slit 45 so that it can rotate within the specified angular range from a first position (filling position) at which a single delivery unit of powdered is metered to a second position (ejecting position) at which the metered powdered is permitted to be ejected.

In this third embodiment, the closure section 4, the fixed stage 10, the gear 20, the ring member 30 and the rotating member 40 are assembled together on concentric circles, the ring member 30 and the rotating member 40 are integrally rotated, so that the rotating member 40 can rotate within the specified angular range from a first position (filling position) at which a single delivery unit of powdered is metered to a second position (ejecting position) at which the metered powdered is permitted to be ejected. In the same manner the ring member 30 is also rotated relative to the fixed stage 10 within the specified angular range.

Figure 12:
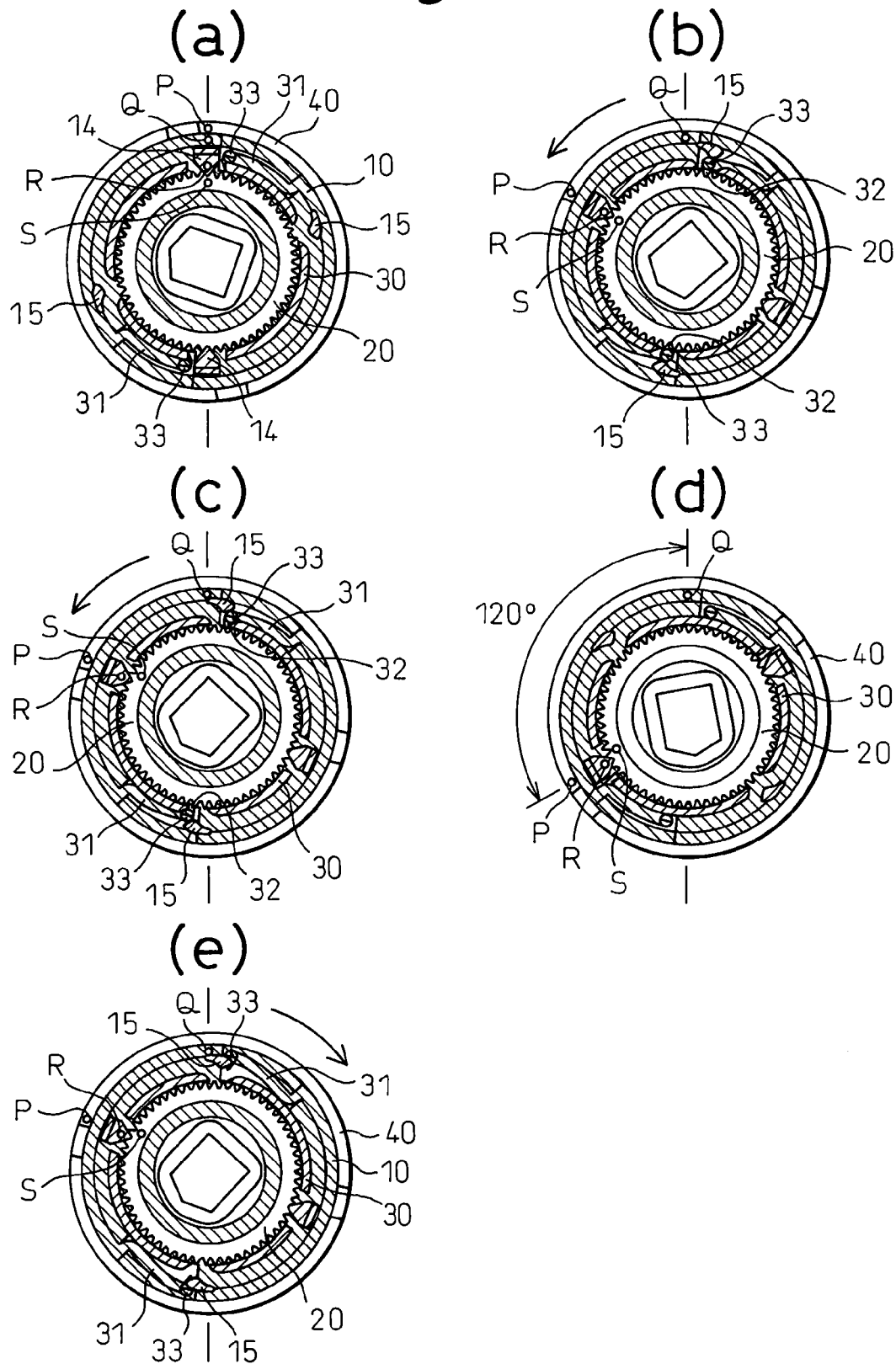
FIG. 12 is a view showing a counter displaying operation in the third embodiment (a)-(e) showing various states of operations.
Figure 13:
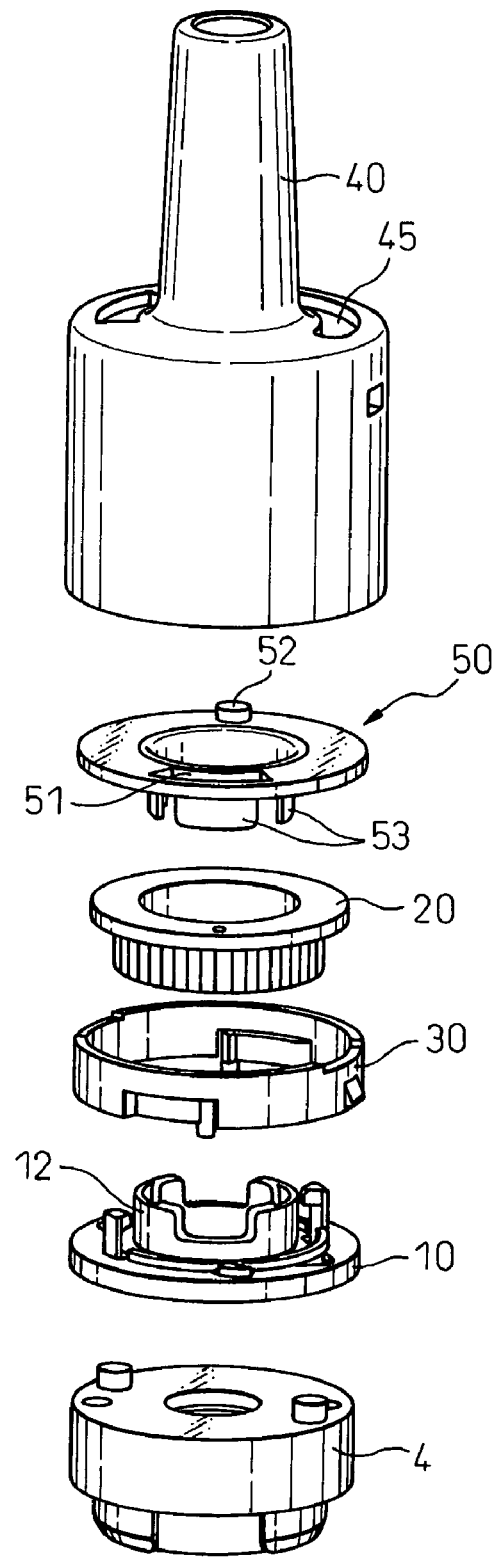
FIG. 13 is a perspective view of the first embodiment including a blind plate.
Figure 14:
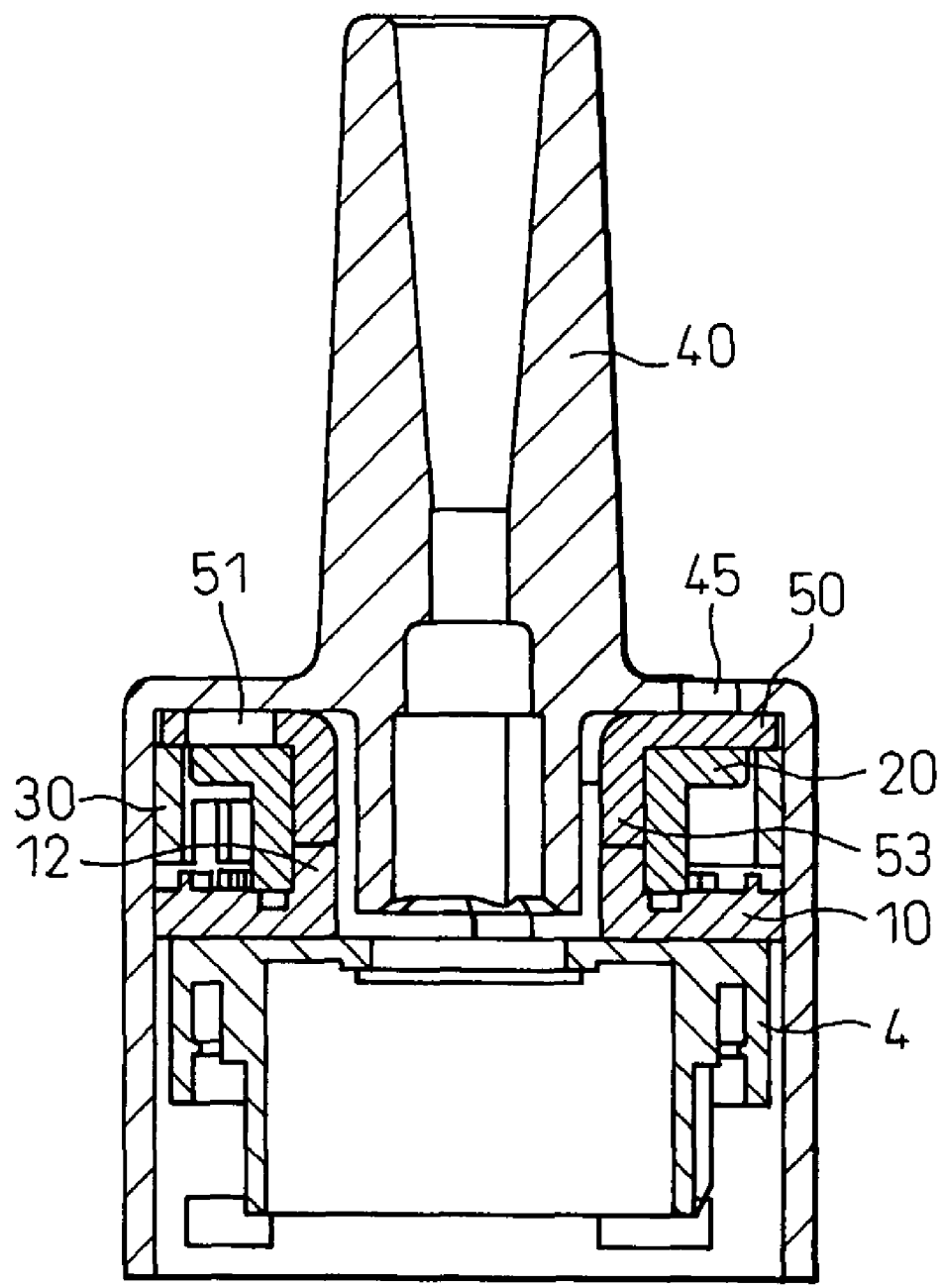
FIG. 14 is a cross-sectional view of the first embodiment including a blind plate.

FIG. 12 shows, in the third embodiment, an operation of count display by rotating the gear at one graduation during the ring member 30 moves from the first position to the second position and returned from the second position to the first position.

FIG. 12(a) shows at the initial (first) position, such as feeding position for powdered medicine. FIG. 12(b) shows the state at which the rotating member is rotated in the direction shown by an arrow and the operation of cam is started. FIG. 12(c) shows the state at which the operation of cam is finished. FIG. 12(d) shows the state at which the rotating member is rotated in the direction shown by an arrow by a predetermined angle (such as 120°), such as the filling (second) position. FIG. 12(e) shows the state at which the rotating member is rotated in the opposite direction, no operation of cam is taken place.

In FIGS. 12(a) to 12(e), from the outside, the reference mark of the rotating member 40, the fixed stage 10, ring member 30 (protrusion 14) and the gear 20 are indicated by round marks P, Q, R and S. In the initial position of FIG. 12(a), the reference marks P, Q, R and S of the respective members is all the same relative to the rotating direction. The fixed stage 10 is not moved regardless to the movements of the ring member 30 (protrusion 14) and the gear 20, the reference mark Q is not changed during the respective steps.

The rotating member 40 and the ring member 30 are rotated together, their reference positions are always at the same position in the rotating direction. As mentioned before, the gear 20 is prevented from being idling relative to the ring member 30 and, therefore, moves in the same manner as the ring member 30 until the gage count indication is proceeded by one graduation, i.e., until the starting point of the cam operation, and the reference position S is the same position and same as P and R in the same rotational direction.

However, the cam lobe 15 of the ring member 30 comes to a position with the protrusion 33 of the cam follower portion at the distal end of the resilient portion of the fixed stage 10 and come into mutually contact the jaw portion 32 at the distal end of the resilient portion 31 is pushed inward. At that time, the jaw portion 32 is engaged with the outer teeth 23 of the gear 20 at the inside of the cam groove 17 of the ring member 30. Thus, the gear 20 is rotated by the jaw portion 32 at a force stronger than the force for preventing idling rotation by the protrusion 14. When the gear 20 is rotated by one tooth or one gage, the protrusion 33 of the cam follower at the distal end of the resilient portion 31 opposite inclined surface of the cam lobe 15 of the ring member 30, the jaw portion 32 is returned radially outward and thus the jaw 32 is disengaged from the outer teeth 23 of the gear 20. Since the gear 20 is prevented from idling by the protrusion 14 of the ring member 30, the gear does not rotate relative to the ring member 30, except for one tooth or one gage. Namely, as shown in FIG. 12 (c), the reference position S of the gear 20 is the position shifted by one gage from the P and R.

Next, at the filling position shown in FIG. 12(d), the rotating member 40 is rotated in the opposite direction, the cam follower portion 33 at the distal end of the resilient portion 31 of the fixed stage comes to the cam lobe 15 of the ring member 30, and at this time, only comes over the cam lobe, although comes into contacts with the opposite face of the cam lobe 15. Namely, the jaw portion 32 at the distal end of the resilient portion 31 moves somewhat in the axial direction of the ring member 30, but does not move in the radial direction, the gear 20 is still prevented from idling relative to the protrusion 14 of the ring member 30.

The other structure and operation of this third embodiment are the same as those of the first embodiment and, therefore, derailed explanation will be omitted. It should be noted that, in the first and second embodiments, same cam operation and function can be used for the respective applications.

The counter mechanism in the feeding device and the feeding device comprising the counter mechanism according to the present invention has been described above with reference to appended drawings showing embodiments thereof. The present invention is by no means limited to above-described embodiments, and various modes, changes and modifications are possible without departing from the spirit and scope of the invention.

INDUSTRIAL APPLICABILITY

Thus, the present invention provides a relatively inexpensively constructed counter mechanism, as well as a metered feeding device comprising the counter mechanism, which is convenient to carry, easy to use, and is capable of accurately administering the powdered medicine in a predetermined amount by spraying or inhalation, which is an excellent effect.

The present invention is especially adapted as a metered feeding device storing in the container, multiple delivery units of the powdered medicine which is administered in a very small amount in each administering operation, and permits the number of already delivered units, and hence remaining amount of the powdered medicine in such a device, to be easily known, and the delivery of the powdered medicine or the like to be performed safely and reliably.

The invention claimed is:

1. A counter mechanism of a feeding device for feeding to the outside, in each discrete feeding operation, an amount corresponding to single delivery unit of stored material which has been stored in a storage chamber, the counter mechanism comprising:
   a fixed member which is fixed to a device body and having a first contact portion formed at a predetermined position in circumferential direction thereof;
   a gear having a count number display that can be monitored from the outside;
   a rotating member being restricted to rotate either to a position in a rotating direction to allow feeding of a single delivery unit and a position to preventing feeding of the stored material;
   a ring member which can rotates in interlock with a rotating motion of said rotating member and comprises a second contact portion formed at a predetermined position in circumferential direction thereof;
   one of the first and second contact portions comprising a resiliently deformable cam follower having a jaw and the other being a cam being engagable with the cam follower, and the gear being controlled to rotate in such a manner that, during the rotating member rotate for a single delivery unit, due to a mutual operation of the cam and cam follower, the jaw is engaged with the gear to rotate the gear only by a single gage in the count number display.

2. A counter mechanism as set forth in claim 1, wherein the rotating member is mounted to be able to rotate only in a positive direction, in the operation of positive rotation, the rotating member can take either a first position in the rotating direction at which feeding of a single delivery unit of the stored material is allowed and a second position at which delivery of the stored material is prevented, during the rotating member moves from the first position to the second position and again from the second position to the first position, the gear is rotated only by a single gage in the count number display.

3. A counter mechanism as set forth in claim 1, wherein the rotating member is rotatable within a range of a predetermined angle between a first position in the rotating direction at which feeding of a single delivery unit of the stored material is allowed and a second position at which delivery of the stored material is prevented, during the rotating member moves for one stroke between the first position and the second position, the gear is rotated only by a single gage in the count number display.

4. A counter mechanism as set forth in claim 1, wherein the first contact portion of the fixed member is a cam follower and the second contact portion of the ring member is a cam.

5. A counter mechanism as set forth in claim 4, wherein the ring member comprises a protrusion being engaged with the gear to prevent the gear from an idling movement thereof except when the gear is moved during the count number display is changed.

6. A counter mechanism as set forth in claim 1, wherein the first contact portion of the fixed member is a cam and the second contact portion of the ring member is a cam follower.

7. A counter mechanism as set forth in claim 1, wherein the fixed member comprises a protrusion being engaged with the gear to prevent the gear from an idling movement thereof except when the gear is moved during the count number display is changed.

8. A counter mechanism as set forth in claim 1, wherein the gear is ring-shaped and comprises a cylinder having an outer surface provided with teeth and a flange integrally formed with the cylinder having a count number display,
   the rotating member comprising a nozzle for the feeding device, a cylinder having a diameter larger than that of the nozzle and adaptable to be rotated for operating the device, and a disc plate integrally formed with and connecting the nozzle and the cylinder and having a window capable of viewing the count number display from the outside through the window.

9. A counter mechanism as set forth in claim 8, wherein the count number display is formed on a face of the flange opposite to the cylinder and the window is provided in the disc plate.

10. A counter mechanism as set forth in claim 1, wherein a thin plate having a small opening for viewing the count number display is disposed between the rotating member and the flange.

11. A counter mechanism as set forth in claim 8, wherein the count number display is formed on a outer wall surface of the flange, and
   the window is provided in the cylinder of the rotating member.

12. A feeding device including the counter as claimed in claim 1, comprising:
   a storage chamber capable of storing multiple delivery units of stored material;
   a container chamber provided on a portion of wall of said storage chamber and capable of containing single delivery unit of the stored material;
   a stored material delivery unit in which the container chamber is allowed to be filled with a single delivery unit of the stored material when a rotating member is in a filling position, and the single delivery unit of the stored material is allowed to be ejected to the outside when the rotating member is in the ejecting position, and
   a pump attached to and connected with the container at the opposite side of the storage chamber through a filter.

13. A feeding device as set forth in claim 12, wherein:
   the container chamber is provided under the bottom of the storage chamber,
   the stored material delivery unit is rotated together with the rotating member so as to be movable between the filling position and the ejecting position, while being kept in contact with a bottom surface of the storage chamber,
   at the filling position, the container chamber is opened relative to the storage chamber by opening an opening means of the stored material delivery unit to allow the container chamber being filled with the stored material from the storage chamber, and at the ejecting position, the container chamber is closed relative to the storage chamber, but communicated with a nozzle formed in the rotating member via a delivery passage of the stored material delivery unit, so that a single delivery unit of stored material in the container chamber is allowed to be ejected to the outside through the delivery passage and the nozzle.

14. A feeding device as set forth in claim 13, wherein a bottom wall of the storage chamber has a hole communicated with the pump and at the filling position the hole communicate the pump to the outside through the delivery passage of the stored material delivery unit and the nozzle of the rotating member and at the ejecting position the hole is close by the stored material delivery unit.

* * * * *